US012016680B2

(12) United States Patent
Adamson et al.

(10) Patent No.: US 12,016,680 B2
(45) Date of Patent: Jun. 25, 2024

(54) SYSTEMS AND METHODS FOR MIDDLE EAR IMMITTANCE TESTING

(71) Applicant: AUDIOPTICS MEDICAL INCORPORATED, Halifax (CA)

(72) Inventors: Robert Adamson, Halifax (CA); Daniel Ryan MacDougall, Dartmouth (CA)

(73) Assignee: AUDIOPTICS MEDICAL INCORPORATED, Halifax Ns (CA)

( * ) Notice: Subject to any disclaimer, the term of this patent is extended or adjusted under 35 U.S.C. 154(b) by 521 days.

(21) Appl. No.: 16/753,258

(22) PCT Filed: Oct. 4, 2018

(86) PCT No.: PCT/CA2018/051255
§ 371 (c)(1),
(2) Date: Apr. 2, 2020

(87) PCT Pub. No.: WO2019/068195
PCT Pub. Date: Apr. 11, 2019

(65) Prior Publication Data
US 2020/0315499 A1    Oct. 8, 2020

Related U.S. Application Data

(60) Provisional application No. 62/568,228, filed on Oct. 4, 2017.

(51) Int. Cl.
*A61B 5/12*    (2006.01)
*A61B 5/00*    (2006.01)
(Continued)

(52) U.S. Cl.
CPC .............. *A61B 5/126* (2013.01); *A61B 5/004* (2013.01); *A61B 5/0066* (2013.01);
(Continued)

(58) Field of Classification Search
CPC .............................. A61B 5/004; A61B 5/0066
(Continued)

(56) References Cited

U.S. PATENT DOCUMENTS

2015/0265189 A1    9/2015  Allen et al.
2017/0251924 A1*   9/2017  Koch ................. A61B 1/00163

FOREIGN PATENT DOCUMENTS

DE           69738629 T2 *  5/2009  ............. A61B 5/121

OTHER PUBLICATIONS

Long-range, wide-field swept source optical coherence tomography with GPU accelerated digital lock in Doppler vibrography for real-time, in vivo middle ear diagnosis, Bio. Optic. Exp. vol. 7, issue 11, 2016 (Year: 2016).*

(Continued)

*Primary Examiner* — Shahdeep Mohammed
*Assistant Examiner* — Marjan Saboktakin
(74) *Attorney, Agent, or Firm* — HILL & SCHUMACHER

(57) ABSTRACT

Acoustic immittance and other characteristics of ears may be determined by measuring eardrum displacements resulting from application of pressure to the eardrum. For example, optical coherence tomography may be applied to monitor eardrum displacements responsive to a sound. The pressure corresponding to the sound is measured by a suitable instrument such as a microphone. The measured displacements and pressures may be processed to obtain a measure of immitance.

23 Claims, 4 Drawing Sheets

(51) Int. Cl.
- *A61B 5/055* (2006.01)
- *A61B 6/03* (2006.01)
- *A61B 8/08* (2006.01)

(52) U.S. Cl.
CPC .............. *A61B 5/0035* (2013.01); *A61B 5/055* (2013.01); *A61B 6/032* (2013.01); *A61B 8/5261* (2013.01)

(58) Field of Classification Search
USPC ........................................................ 600/427
See application file for complete search history.

(56) References Cited

OTHER PUBLICATIONS

MacDougall et al., "Long-range, wide-field swept-source optical coherence tomography with GPU accelerated digital lock-in Doppler vibrography for real-time, in vivo middle ear diagnostics", Biomedical Optics Express, vol. 7, No. 11, Nov. 1, 2016, pp. 4621-4635, published Oct. 18, 2016.

MacDougall et al., Clinical Doppler-Mode Optical Coherence Tomography of the Middle Ear, AIP Conference Proceedings 1965, 110001, May 2018 ; pp. 110001-1-110001-6.

Jeon et al., In Vivo Vibration Measurement of Middle Ear Structure Using Doppler Optical Coherence Tomography: Preliminary Study, Clinical and Experimental Otorhinolaryngology, Jul. 27, 2018 ; pp. 1-10.

MacDougall et al., "Real-time swept-source Doppler optical coherence tomography for middle ear diagnostics", Frontiers in Optics 2015, OSA Technical Digest (Optical Society of America, 2015), paper FW4E.3. San Jose, California United States, Oct. 18-22, 2015 ; 2 pages.

Sylwestrzak et al., "Four-dimensional structural and Doppler optical coherence tomography imaging on graphics processing units", Journal of Biomedical Optics, vol. 17(10), Oct. 2012, pp. 100502-1 to 100502-3, published online Oct. 5, 2012 +.

Huang et al., "Real-time 3D and 4D Fourier domain Doppler optical coherence tomography based on dual graphics processing units", Biomedical Optics Express, vol. 3, No. 9, Sep. 1, 2012; pp. 2162-2174, published Aug. 20, 2012.

International Search Report of the parent PCT application PCT/CA2018/051255 filed Oct. 4, 2018 . The mail date of search report is Jan. 14, 2019.

\* cited by examiner

SYSTEMS AND METHODS FOR MIDDLE EAR IMMITTANCE TESTING

CROSS-REFERENCE TO RELATED APPLICATION

This application is a National Phase application claiming the benefit of the international PCT Patent Application No. PCT/CA2018/051255, filed on Oct. 4, 2018, in English, which claims priority to U.S. Provisional Application No. 62/568,228, titled "SYSTEMS AND METHODS FOR MIDDLE EAR IMMITTANCE TESTING" and filed on 4 Oct. 2017, the entire contents of which are incorporated herein by reference.

FIELD

This invention relates to methods and apparatus for performing immittance testing of ears.

BACKGROUND

The middle ear is made up of the eardrum and a set of structures whose main physiological purpose is to transmit sound vibrations from the eardrum to the cochlea. Conductive hearing loss occurs when the middle ear is unable to perform this function at a normal level.

A wide range of disorders can cause conductive hearing loss. The majority of these involve either a fixation or a discontinuity in the transmission pathway for vibrations. For example, otosclerosis is a disease in which a plaque forms on one middle ear structure, the stapes, which prevents it from vibrating, causing a conductive hearing loss. Ossicular erosion is a process by which the ossicles, the three bones that mechanically connect the eardrum to the cochlea, erode away, eventually creating a discontinuity in the vibration pathway. This also leads to conductive hearing loss.

While conductive hearing loss can often be treated with surgery, for instance by the implantation of a prosthetic to replace a defective ossicle, the cause of a conductive hearing loss can be difficult to diagnose clinically. Many diseases that cause conductive loss such as otosclerosis leave no clear signature in CT scans or through microscopic examination of the eardrum (two main clinical imaging modalities presently used to image the ear). Moreover, even when effects of a disease are apparent in imaging, the degree to which it affects hearing cannot be discerned from imaging alone. For this reason, otologists rely on a battery of functional middle ear tests in addition to imaging to diagnose middle ear problems.

One subset of these tests are collectively known as acoustic immittance tests. Immittance tests provide objective information about the mechanical impedance of the ear as seen from the ear canal. Mechanical impedance Z can be defined as the ratio of pressure P to volumetric velocity $V_s$ which can be expressed as:

$$Z = \frac{P}{V_S}. \quad (1)$$

Mechanical impedance of the middle ear can roughly be thought of as a measure of "stiffness" of the middle ear. An eardrum will move relatively little in response to a given amount of pressure when the middle ear presents a high mechanical impedance. An eardrum will move relatively freely in response to a given amount of pressure when the middle ear presents a low mechanical impedance.

One benefit of immittance testing for diagnosing conductive hearing loss is that ears in which some part of the mechanical pathway between the eardrum and the cochlea is fixed will have a higher-than-normal mechanical impedance. Conversely, ears in which there is a disruption in the mechanical pathway can exhibit lower-than-normal mechanical impedance.

Traditional methods of acoustic impedance measurement rely on having a calibrated sound source with a known acoustic output impedance. The impedance of the middle ear is derived from the measured pressure generated in the ear canal by the sound source, the stimulus strength, and the acoustic impedance of the sound source.

Acoustic immittance is typically measured via a technique called tympanometry. In tympanometry, an assembly that includes a pressurization tube, a microphone, and a sound source is inserted into the ear canal. The assembly is surrounded by an earpiece that forms an acoustic seal with the ear canal. The pressurization tube applies a quasi-static pressure to the ear canal while the sound source, which has a known acoustic output impedance, generates a tone at one or more frequencies (typically 226 Hz). The microphone records the pressure in the ear canal. From the impedance of the source, the stimulus strength, and the measured pressure, the acoustic impedance (or equivalently, the admittance, the inverse of the impedance) is obtained. The impedance of the middle ear is a function of the pressure difference across the eardrum and so different impedance results are obtained as the quasi-static pressure is varied over a range of a few kilopascals. In a normal ear the impedance will be minimal and the admittance maximal when the pressure difference across the tympanic membrane is close to zero.

While tympanometry is the most common immittance test in clinical practice, other methods are also used for measuring immittance. In wideband Middle Ear Power Analysis, a sound source with a known acoustic output impedance and a microphone are inserted in the ear. The sound source frequency is swept over a wide range (e.g. 20 Hz to 20 KHz, the accepted "range of human hearing") and the acoustic reflectance, a quantity mathematically equivalent to the middle ear impedance, is calculated as a function of frequency [1].

Two other common audiometric tests related to immittance testing are the acoustic reflex threshold test and the acoustic reflex decay test. The acoustic reflex is a protective reflex of the stapedius muscle that contracts in response to the presentation of a loud sound. The contraction of this muscle effectively stiffens the stapes and can be observed as an increase in impedance in tympanometry and other immittance tests. The acoustic reflex threshold test measures softest sound that elicits a stapes reflex response, while the acoustic reflex decay test measures the amount of decay in the increased stiffness over a set time window (usually 10 s). Because the stapedius muscle is innervated by the facial nerve, the acoustic reflex threshold and acoustic reflex decay can indicate problems associated with neuromas or other nerve disorders affecting the cochlear nerves, particularly nerves VII and VIII [2], [3].

Optical coherence tomography (OCT) is an optical imaging modality that uses optical interferometry. OCT may be applied to obtain depth-resolved images of tissue.

SUMMARY

This invention has a number of aspects. These include without limitation:
- methods for acoustic immitance testing;
- methods for processing output signals from a system monitoring movements of an eardrum to yield acoustic immitance values;
- apparatus for acoustic immitance testing;
- apparatus for processing output signals from a system monitoring movements of an eardrum to yield acoustic immitance values;
- a Doppler OCT system; and
- a processor connected to receive output signals from the Doppler OCT system, the output signals comprising information that directly or indirectly indicates displacements and velocities for points on the eardrum surface, and where the processor is configured to process the signals to yield the volume displacement or volume velocity of the eardrum and, by extension, acoustic immitance values.

One aspect of the invention provides a system including an optical coherence tomography imaging system configured to image a surface being induced into motion by a sound stimulus, the imaging system operable to measure a phase and amplitude of the motion of the surface in a spatially resolved way. The system also includes a microphone operable to measure a pressure of the sound stimulus on the surface and a processor configured to calculate a volume velocity of the surface by integrating the contribution to the volume velocity made by the motion of the surface at a plurality of locations on the surface.

The surface may be an eardrum.

The system may include a device for applying a quasi-static pressure to an ear canal and an earpiece that creates an acoustic seal with the ear canal. In some embodiments, the system is configured to report a change in the volume velocity or acoustic impedance as the quasi-static pressure is varied.

The system may include a speaker configured to emit a sound stimulus operative to elicit an acoustic reflex response, the system may be configured to measure a change in acoustic impedance resulting from the acoustic reflex response.

The system may include a speaker configured to emit a sound stimulus operative to elicit an acoustic reflex response, the system may be configured to measure motion of at least one of a malleus, incus, stapes and stapedius tendon when the acoustic reflex response is active.

The sound stimulus may be sinusoidal.

The sound stimulus may be a broadband stimulus.

The broadband stimulus may include one of clicks, white noise and signals including a sum of sine waves at multiple frequencies.

The system may be configured to monitor a decay in an acoustic impedance increase caused by the acoustic reflex over time.

The system may include a pump controllably coupled to the processor, the pump may be configured to maintain a static pressure in an ear canal.

The optical coherence tomography imaging system may include one of a swept-source laser and a broadband light source.

The swept-source laser may be synchronized with a sweep clock signal, the sweep clock signal may synchronize the laser with an acoustic phase of the sound stim ulus.

The optical coherence tomography imaging system may be configured to perform combined structural optical coherence tomography and Doppler optical coherence tomography.

The processor may be configured to process signals from an interferometer to produce an interferogram representing one or both of an ear canal and the surface.

The processor may be configured to extract structural optical coherence tomography data from a computed magnitude of a discrete Fourier transform of the interferogram.

The processor may be configured to extract Doppler optical coherence tomography data from the interferogram using a digital lock-in detection method.

The processor may be configured to determine a plurality of voxels lying on the surface using the structural optical coherence tomography data, determine Doppler vibration displacement amplitude and phase for each of the plurality of voxels using the Doppler optical coherence tomography data, determine a plurality of spatially resolved individual displacements, each of the plurality of individual displacements corresponding to an individual displacement of one of the plurality of voxels induced by the sound stimulus, and integrate over the plurality of spatially resolved individual displacements.

The plurality of voxels may correspond to a portion of the surface that includes the umbo at which the tympanic membrane is coupled to an ossicular chain of an ear. In some embodiments, the portion of the surface excludes 70%±26% of the surface.

The plurality of voxels may correspond to an observable portion of the surface.

In some embodiments, the observable portion of the surface may correspond to at least 20% of the surface.

The processor may be configured to scale the volume velocity using a calibration factor, the calibration factor determined using tympanometry data obtained from a plurality of ears.

The processor may be configured to perform parametric fitting to fit the plurality of voxels on the surface. In some embodiments, the parametric fitting is a polynomial least-squares fitting.

The processor may be configured to apply a smoothing algorithm to remove noise from the structural optical coherence data.

The processor may be configured to determine a local surface normal vector for each of the plurality of voxels.

The processor may be configured to determine the local surface normal vector for each of the plurality of voxels by one of using a parametric model and numerically calculating the local surface normal for each of the plurality of voxels.

Numerically calculating the local surface normal for each of the plurality of voxels may include using a gradient kernel.

One or more of the spatially resolved displacements may be corrected by dividing the displacement by a cosine of an angle between the local surface normal vector for one of the voxels corresponding to the spatially resolved displacement and an optical line direction.

The processor may be configured to apply regularization to reduce an effect of noise.

The optical coherence topography system may include a laser Doppler vibrometry imaging system.

The processor may be configured to determine a three-dimensional shape of the surface using data obtained from at least one of a computed tomography scan, an ultrasound scan, a magnetic resonance imaging scan and an image processing technique that constructs a three-dimensional model from a plurality of two-dimensional images.

The processor may be configured to make data accessible for reference, the data comprising at least one of an acoustic impedance, structural optical coherence topography data and Doppler optical coherence topography data. In some embodiments, the processor may be configured to one or more of display the data using a display, store the data in a data store and print the data using a printer.

The system may include an imaging head, the imaging head connected to transmit and detect light for the optical coherence topography imaging system and may include one or more tubes for carrying the sound stimulus and one or more tubes acoustically coupled to the microphone.

The imaging head may include a handheld endoscope dimensioned for insertion into an ear canal. In some embodiments, the endoscope includes a disposable speculum.

The imaging head may be integrated into a surgical microscope.

The imaging head may be fixed to a frame configured to stabilize a patient's head.

The system may include a display, the system may be configured to display on the display in real time images of the surface.

The processor may be configured to perform imaging simultaneously with acoustic impedance measurement.

Another aspect of the invention provides a system for measuring an acoustic impedance of a middle ear of an ear. The system includes an audio source operable to generate a sound stimulus, the sound stimulus effective to induce motion of an eardrum of the ear, an optical detection modality configured to measure displacements at points of a two-dimensional array of points on the eardrum in response to the sound stimulus and a microphone operable to measure pressure of the sound stimulus on the ear drum. The system also includes a processor, the processor configured to calculate a volume velocity of the eardrum by integrating the displacement over the eardrum, and calculate the acoustic impedance of the middle ear as a ratio of the measured pressure of the sound stimulus on the ear drum to the volume velocity.

The system may include a pump controllably coupled to the processor, the pump configured to maintain a static pressure in an ear canal of the ear.

The optical detection modality may include an optical coherence tomography imaging system.

The optical coherence tomography imaging system may include a swept-source laser or a broadband light source.

The swept-source laser may be synchronized with a sweep clock signal, the sweep clock signal synchronizing the laser with an acoustic phase of the sound stimulus.

The optical coherence tomography imaging system may be configured to perform combined structural optical coherence tomography and Doppler optical coherence tomography.

The processor may be configured to process signals from an interferometer to produce an interferogram representing one or both of an ear canal of the ear and the eardrum.

The processor may be configured to extract structural optical coherence tomography data from a computed magnitude of a discrete Fourier transform of the interferogram.

The processor may be configured to extract Doppler optical coherence tomography data from the interferogram using a digital lock-in detection method.

The processor may be configured to determine a plurality of voxels lying on a surface of the eardrum using the structural optical coherence tomography data, determine vibration displacement amplitude and phase for each of the plurality of voxels using the Doppler optical coherence tomography data, determine a plurality of spatially resolved individual displacements, each of the plurality of individual displacements corresponding to an individual displacement of one of the plurality of voxels induced by the sound stimulus, and integrate over the plurality of spatially resolved individual displacements.

The plurality of voxels may correspond to a portion of the eardrum that includes the umbo at which the ossicular chain of the ear is coupled to the eardrum. In some embodiments, the portion of the eardrum may exclude 70%±26% of the surface of the eardrum.

The plurality of voxels may correspond to an observable portion of the eardrum. In some embodiments, the observable portion of the eardrum may correspond to at least 20% of the eardrum.

The processor may be configured to scale the volume velocity using a calibration factor, the calibration factor determined using tympanometry data obtained from a plurality of ears.

The processor may be configured to perform parametric fitting to fit the plurality of voxels on the surface of the eardrum. In some embodiments, the parametric fitting includes polynomial least-squares fitting.

The processor may be configured to apply a smoothing algorithm to remove noise from the structural optical coherence data.

The processor may be configured to determine a local surface normal vector for each of the plurality of voxels.

The processor may be configured to determine the local surface normal vector for the surface of the eardrum by one of using a parametric model and numerically calculating the surface normal. In some embodiments, numerically calculating the surface normal includes using a gradient kernel.

One or more of the spatially resolved displacements may be corrected by dividing the displacement by a cosine of an angle between the local surface normal vector for one of the voxels corresponding to the spatially resolved displacement and an optical line direction.

The processor may be configured to apply regularization to reduce an effect of noise on the spatially resolved displacements.

The sound stimulus may have a magnitude of 90 dBSPL±10% at 500 Hz.

The sound stimulus may be sinusoidal.

The sound stimulus may be a broadband stimulus. In some embodiments, the broadband stimulus includes one of clicks, white noise, and signals comprising a sum of sine waves at multiple frequencies.

The optical detection modality may include a laser Doppler vibrometry imaging system.

The processor may be configured to determine a structure of the eardrum using data obtained from at least one of a computed tomography scan, an ultrasound scan, a magnetic resonance imaging scan and an image processing technique that constructs a three dimensional model from a plurality of two dimensional images.

The optical detection modality may include a swept-source laser, the swept-source laser operating in synchrony with a sweep clock signal. The optical detection modality may also include a scanner, the scanner operable to scan a beam emitted by the laser across the eardrum. The audio source and the scanner may be synchronized to the sweep clock signal such that an acoustic phase of the acoustic stimulus is advanced in coordination with each sweep of the laser.

The processor may be configured to make data accessible for reference, the data may include at least one of the acoustic impedance, structural optical coherence topography data and Doppler optical coherence topography data.

The processor may be configured to one or more of display the data using a display, store the data in a data store and print the data using a printer.

The system may include an imaging head, the imaging head connected to transmit and detect light for the optical detection modality and including a sound outlet for the sound stimulus and a pickup for providing the pressure of the sound stimulus on the ear drum to the microphone.

The imaging head includes a handheld endoscope insertable into an ear canal. In some embodiments, the endoscope comprises a disposable speculum.

The imaging head may be integrated into a surgical microscope.

The imaging head may be fixed to a frame configured to stabilize a patient's head.

The system may include a display. The system may be configured to display on the display in real time images of the eardrum surface.

The processor may be configured to perform imaging simultaneously with acoustic impedance measurement.

Another aspect of the invention provides a method, the method including inducing motion of a surface by applying a sound stimulus to the surface. The method also includes with an optical coherence tomography imaging system, imaging the surface being induced into motion by the sound stimulus, the imaging operable to measure a phase and amplitude of the motion of the surface in a spatially resolved way. The method also includes measuring pressure of the sound stimulus on the surface, and by an electronic data processor, calculating a volume velocity of the surface by integrating contributions to the volume velocity made by the motion of the surface at a plurality of locations on the surface.

The surface may be an eardrum.

The method may include sealing an ear canal, applying a quasi-static pressure to the ear canal and reporting a change in the volume velocity or acoustic impedance as a function of the quasi-static pressure.

The method may include triggering an acoustic reflex response and measuring a change in acoustic impedance resulting from the acoustic reflex response.

The method may include emitting a sound stimulus operative to elicit an acoustic reflex response and measuring motion of at least one of a malleus, incus, stapes and stapedius tendon when the acoustic reflex response is active.

The sound stimulus may be sinusoidal.

The sound stimulus may be a broadband stimulus. In some embodiments, the broadband stimulus includes one of clicks, white noise and signals comprising a sum of sine waves at multiple frequencies.

The method may include monitoring a decay in an acoustic impedance increase caused by the acoustic reflex over time.

The method may include controlling a static pressure in an ear canal by the electronic data processor.

The optical coherence tomography imaging system may include one of a swept-source laser and a broadband light source.

The method may include synchronizing the swept-source laser with a sweep clock signal, the sweep clock signal synchronizing the laser with an acoustic phase of the sound stimulus.

The method may include performing combined structural optical coherence tomography and Doppler optical coherence tomography to determine the phase and amplitude of the motion of the surface using the optical coherence tomography imaging system.

The method may include processing signals from an interferometer to produce an interferogram representing one or both of an ear canal and the surface.

The method may include extracting structural optical coherence tomography data from a computed magnitude of a discrete Fourier transform of the interferogram.

The method may include extracting Doppler optical coherence tomography data from the interferogram using a digital lock-in detection method.

The method may include determining a plurality of voxels lying on the surface using the structural optical coherence tomography data, determining Doppler vibration displacement amplitude and phase for each of the plurality of voxels using the Doppler optical coherence tomography data, determining a plurality of spatially resolved individual displacements, each of the plurality of individual displacements corresponding to an individual displacement of one of the plurality of voxels induced by the sound stimulus, and integrating over the plurality of spatially resolved individual displacements.

The plurality of voxels may correspond to a portion of the surface coupled to an ossicular chain of an ear at an umbo of the ear. In some embodiments, the portion of the surface excludes 70%±26% of the surface.

The plurality of voxels may correspond to an observable portion of the surface. In some embodiments, the observable portion of the surface corresponds to at least 20% of the surface.

The method may include scaling the volume velocity using a calibration factor, the calibration factor determined using tympanometry data obtained from a plurality of ears.

The method may include performing parametric fitting to fit the plurality of voxels on the surface.

The parametric fitting may be a polynomial least-squares fitting.

The method may include applying a smoothing algorithm to remove noise from the structural optical coherence data.

The method may include determining a local surface normal vector for each of the plurality of voxels.

The method may include determining the local surface normal vector for each of the plurality of voxels by one of using a parametric model and numerically calculating the local surface normal for each of the plurality of voxels.

Numerically calculating the local surface normal for each of the plurality of voxels may include using a gradient kernel.

The method may include correcting one or more of the spatially resolved displacements by dividing the displacement by a cosine of an angle between the local surface normal vector for one of the voxels corresponding to the spatially resolved displacement and an optical line direction.

The method may include applying regularization to reduce an effect of noise on the spatially resolved displacements.

The optical coherence tomography imaging system may include a laser Doppler vibrometry imaging system.

The method may include determining a structure of the surface using data obtained from at least one of a computed tomography scan, an ultrasound scan, a magnetic resonance imaging scan and an image processing technique that constructs a three dimensional model from a plurality of two dimensional images.

The method may include making data accessible for reference, the data comprising at least one of an acoustic impedance, structural optical coherence topography data and Doppler optical coherence topography data.

The method may include one or more of displaying the data using a display, storing the data in a data store and printing the data using a printer.

The method may include inserting an imaging head into a subject's ear canal, the imaging head connected to transmit and detect light for the optical coherence tomography imaging system and comprising a sound outlet for the sound stimulus and a pickup for detecting the pressure of the sound stimulus on the surface.

The imaging head may include a handheld endoscope insertable into an ear canal. In some embodiments, the endoscope includes a disposable speculum.

The imaging head may be integrated into a surgical microscope.

The imaging head may be fixed to a frame and the method may include applying the frame for stabilizing a subject's head.

The method may include displaying in real time images of the eardrum and/or an ear canal obtained by way of the imaging head while aligning the imaging head.

The method may include performing imaging simultaneously with measuring acoustic impedance.

Another aspect of the invention provides a method for measuring acoustic impedance of a middle ear of an ear. The method includes inducing motion of an eardrum of the ear by applying a sound stimulus to the ear, measuring displacements of the eardrum caused by the sound stimulus at points of a two-dimensional array of points on the eardrum using an optical detection modality and measuring pressure of the sound stimulus on the ear drum. The method also includes by an electronic data processor calculating the acoustic impedance of the middle ear by steps including calculating a volume velocity of the eardrum by integrating the displacement over the eardrum, and determining a ratio of the measured pressure of the sound stimulus on the ear drum to the volume velocity.

The method may include controlling a pressure in an ear canal of the ear to maintain a desired static pressure under control of the processor.

The optical detection modality may include optical coherence tomography.

The optical coherence tomography may be performed using an optical coherence tomography imaging system comprising one of a swept-source laser and a broadband light source.

The method may include synchronizing the swept-source laser with a sweep clock signal, the sweep clock signal synchronizing the laser with an acoustic phase of the sound stimulus.

The method may include performing combined structural optical coherence tomography and Doppler optical coherence tomography.

The method may include processing signals from an interferometer to produce an interferogram representing one or both of an ear canal of the ear and the eardrum.

The method may include extracting structural optical coherence tomography data from a computed magnitude of a discrete Fourier transform of the interferogram.

The method may include extracting Doppler optical coherence tomography data from the interferogram using a digital lock-in detection method.

The method may include determining a plurality of voxels lying on a surface of the eardrum using the structural optical coherence tomography data, determining vibration displacement amplitude and phase for each of the plurality of voxels using the Doppler optical coherence tomography data, determining a plurality of spatially resolved individual displacements, each of the plurality of individual displacements corresponding to an individual displacement of one of the plurality of voxels induced by the sound stimulus, and integrating over the plurality of spatially resolved individual displacements.

The plurality of voxels may correspond to a portion of the eardrum coupled to an ossicular chain of the ear at an umbo of the ear. In some embodiments, the portion of the eardrum excludes 70%±26% of the surface of the eardrum.

The plurality of voxels may correspond to an observable portion of the eardrum. In some embodiments, the observable portion of the eardrum corresponds to at least 20% of the eardrum.

The method may include scaling the volume velocity using a calibration factor, the calibration factor determined using tympanometry data obtained from a plurality of ears.

The method may include performing parametric fitting to fit the plurality of voxels on the surface of the eardrum.

The parametric fitting may include polynomial least-squares fitting.

The method may include applying a smoothing algorithm to remove noise from the structural optical coherence data.

The method may include determining a local surface normal vector for the surface of the eardrum at each of the plurality of voxels.

The method may include determining the local surface normal vector for the surface of the eardrum by one of using a parametric model and numerically calculating the surface normal.

Numerically calculating the surface normal may include applying a gradient kernel.

The method may include correcting one or more of the spatially resolved displacements by dividing the displacement by a cosine of an angle between the local surface normal vector for one of the voxels corresponding to the spatially resolved displacement and an optical line direction.

The method may include applying regularization to reduce the effect of noise on the spatially resolved displacements.

The sound stimulus may have a magnitude of 90 dBSPL±10% at 500 Hz.

The sound stimulus may be sinusoidal.

The sound stimulus may be a broadband stimulus. In some embodiments, the broadband stimulus includes one of clicks, white noise, and signals comprising a sum of sine waves at multiple frequencies.

The optical detection modality may include a laser Doppler vibrometry imaging system.

The method may include determining a structure of the eardrum using data obtained from at least one of a computed tomography scan, an ultrasound scan, a magnetic resonance imaging scan and an image processing technique that constructs a three dimensional model from a plurality of two dimensional images.

The optical detection modality may include a swept-source laser, the swept-source laser operating in synchrony with a sweep clock signal. The optical detection modality may also include a scanner, the scanner operable to scan a beam emitted by the laser across the eardrum. The audio source and the scanner may be synchronized to the sweep clock signal such that an acoustic phase of the acoustic stimulus is advanced in coordination with each sweep of the laser.

The method may include making data accessible for reference, the data comprising at least one of the acoustic impedance, structural optical coherence topography data and Doppler optical coherence topography data.

The method may include one or more of displaying the data using a display, storing the data in a data store and printing the data using a printer.

The method may include inserting an imaging head into a subject's ear canal, the imaging had connected to transmit and detect light for the optical imaging modality and comprising a sound outlet for the sound stimulus and a pickup for detecting the pressure of the sound stimulus on the eardrum.

The imaging head may include a handheld endoscope. In some embodiments, the endoscope includes a disposable speculum.

The imaging head may be integrated into a surgical microscope.

The imaging head may be fixed to a frame and the method may include applying the frame to stabilize a subject's head.

The method may include displaying in real time images of the eardrum and/or an ear canal obtained by way of the imaging head while aligning the imaging head.

The method may include performing imaging of the ear drum simultaneously with measuring acoustic impedance.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

The present invention provides systems and methods useful for measuring acoustic immittance and other characteristics of ears. In some embodiments, the systems and methods process measurements of eardrum displacement resulting from application of pressure to the eardrum. For example, OCT may be applied to monitor eardrum displacements.

Measured eardrum displacements may be used in the performance of acoustic immittance tests including one or more of tympanometry, middle ear power analysis, acoustic reflex threshold tests, and acoustic reflex decay tests, for example.

Some example embodiments provide methods for determining the acoustic impedance of the middle ear that involve using Doppler OCT or another optical detection modality such as Laser Doppler Vibrometry (LDV) to measure the motion of the surface of the eardrum and to calculate the volume velocity of the eardrum as an integrated displacement over that surface. The ratio of the sound pressure at the eardrum (as measured by a microphone) to the volume velocity yields the impedance.

OCT may be applied to image the middle ear volume through the intact tympanic membrane as described, for example, in reference [4], which is hereby incorporated herein by reference for all purposes. Using an OCT system like that described in reference [4], it is also possible to analyze the phase of the interferometric signal in order to measure the motion of each pixel in an image in response to sound [4]. This is called Doppler OCT.

Figure 1:
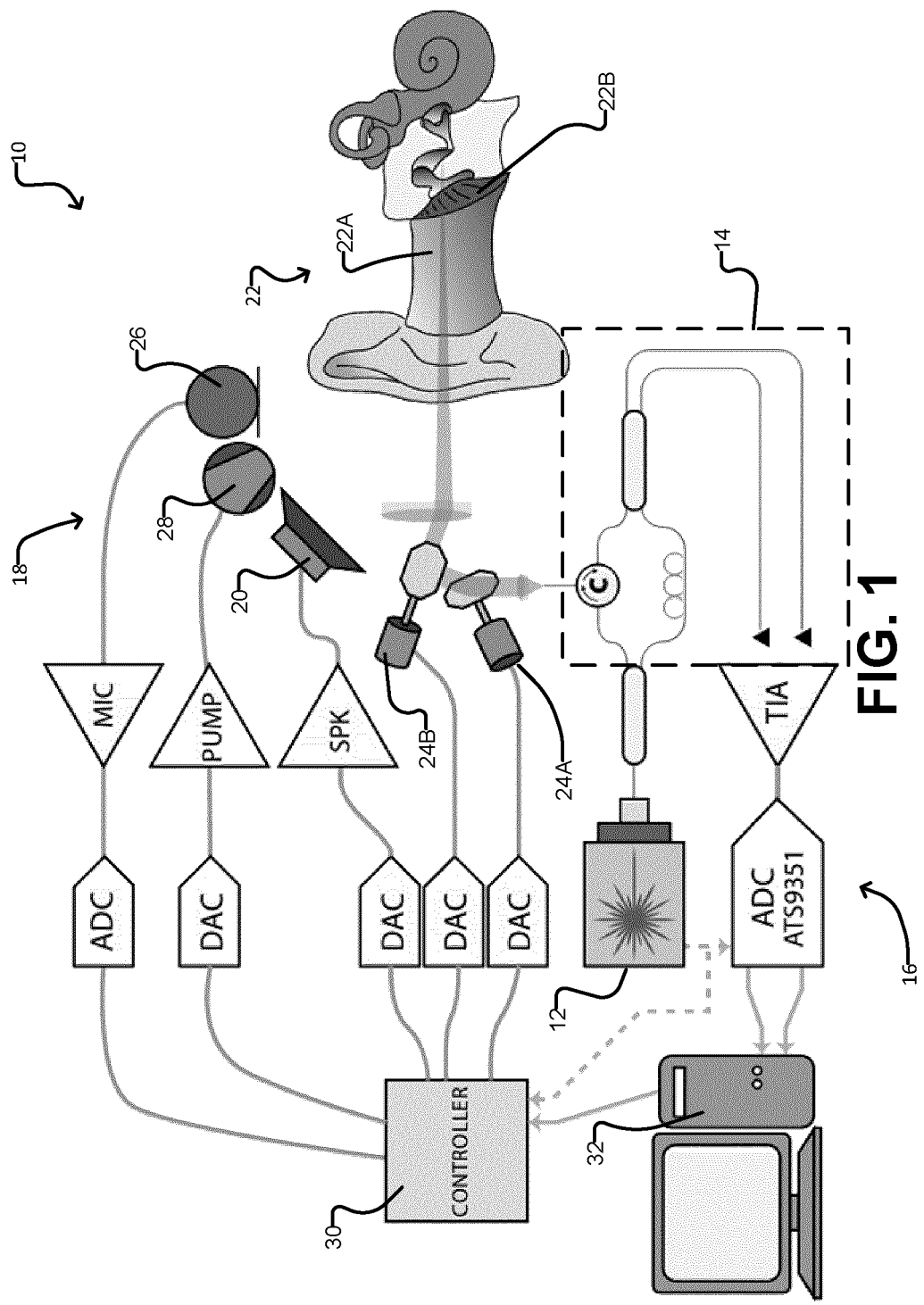
FIG. 1 is a block diagram of a Doppler OCT system according to an example embodiment of the invention.

For example, combined structural OCT and Doppler OCT may be performed using the system shown in FIG. 1. FIG. 1 shows a Doppler OCT system 10 which comprises an akinetic swept-source laser 12, an interferometer 14, high speed digitization electronics 16, and a system 18 for delivering a sound stimulus to an ear 22 via a speaker 20. The sound stimulus provided by speaker 20, and scanning mirrors 24A and 24B, are synchronized to a sweep clock signal of laser 12 in such a way that the acoustic phase of the stimulus is advanced in coordination with each sweep of laser 12. The sweep clock signal is a clock signal generated by laser 12 or used to drive laser 12 such that an edge of the sweep clock signal occurs in a fixed timing relationship to the beginning of the frequency sweep of laser 12. Synchronization of the sweep clock signal and sound stimulus ensures that the measured optical phase in the resulting image of ear 22 will advance at the same rate as the phase of the acoustic stimulus resulting in a stable phase shift between the acoustic stimulus and the measured optical phase at each voxel in the image.

Microphone 26 records the pressure in ear canal 22A in response to the sound stimulus generated by speaker 20.

A pump 28 may be provided to maintain a desired static pressure in ear canal 22A.

Speaker 20, scanning mirrors 24A, 24B, microphone 26, and pump 28 may all be connected to a controller 30, which in turn may be connected to a computer or other suitable processor 32. Laser 12 is also connected to processor 32, and may also be controlled by controller 30 as shown for example in FIG. 1. In some embodiments controller 30 is a module implemented on, and/or forming a part of, processor 32.

Processor 32 may process signals from interferometer 14 to produce an interferogram representing ear canal 22A and/or eardrum 22B.

Structural data may be extracted from the magnitude of the discrete Fourier transform of the interferogram as in conventional swept-source OCT imaging. A Fourier transform may be performed for each laser beam location to produce a depth-resolved image line. Scanning mirrors 24A and 24B may scan the beam from laser 12 laterally across the field of view.

Doppler data may be extracted through a digital lock-in detection method wherein for each lateral location, the phase of the discrete Fourier transform of the measured interferogram is multiplied by a calculated phasor $e^{2\pi i f t}$ at each voxel along the image line. The calculated phasor evolves at the acoustic frequency f which, being locked to the sweep clock signal of laser 12, advances at the same rate as the phase of the discrete Fourier transform of the interferogram for all voxels in the image. The product of the phasor and the discrete Fourier transform phase at each voxel may be averaged over time to produce a high signal-to-noise ratio estimate of the vibration amplitude at each voxel. An example OCT system of a type that may be used in implementations of the present invention is described in more detail in reference [4].

Figures 2A, 2B:
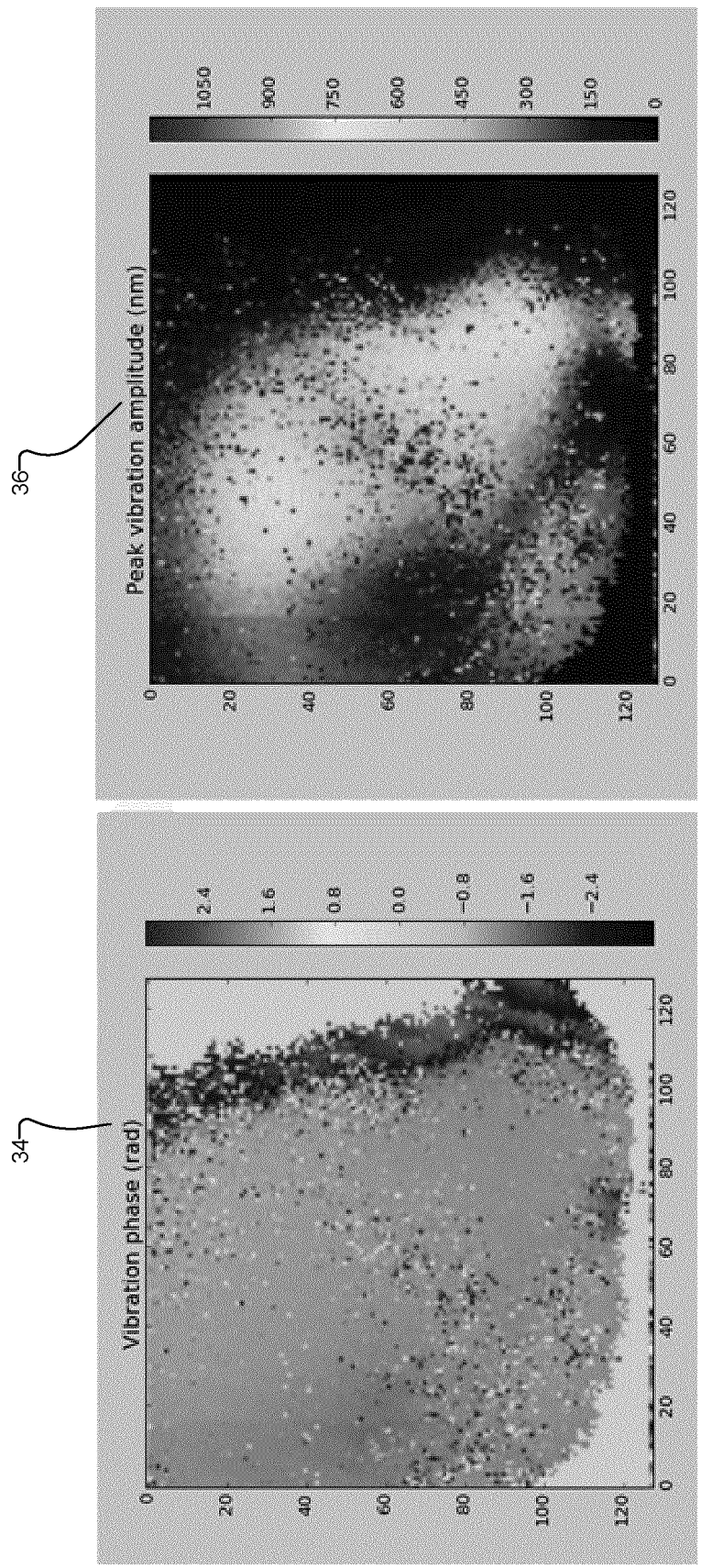
FIGS. 2A and 2B are 2D plots showing phase and amplitude, respectively, of vibration measured at the surface of the eardrum using Doppler-mode OCT on a human cadaveric ear at 500 Hz and 90 dBSPL.

FIGS. 2A and 2B show an example plot 34 of the measured phase and an example plot 36 of the amplitude, respectively, of vibration at the surface of eardrum 22B measured using Doppler-mode OCT on a human cadaveric ear at 500 Hz and 90 dBSPL.

Figure 3:
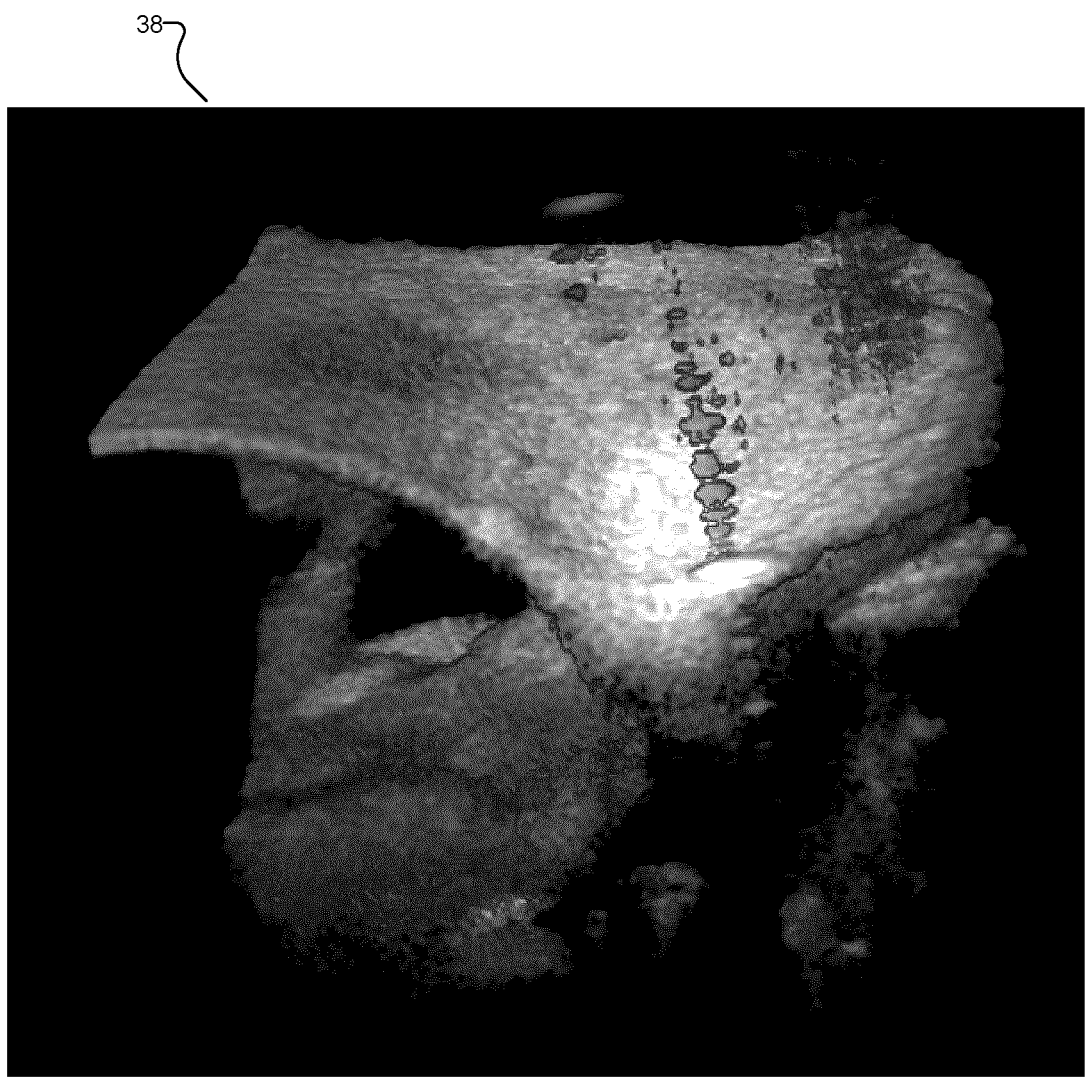
FIG. 3 is a 3D volume render of the ear used in the measurement of FIGS. 2A and 2B.

Simultaneously-acquired structural OCT data of an ear was used to produce the 3D volume render 38 shown in FIG. 3.

Figure 4:
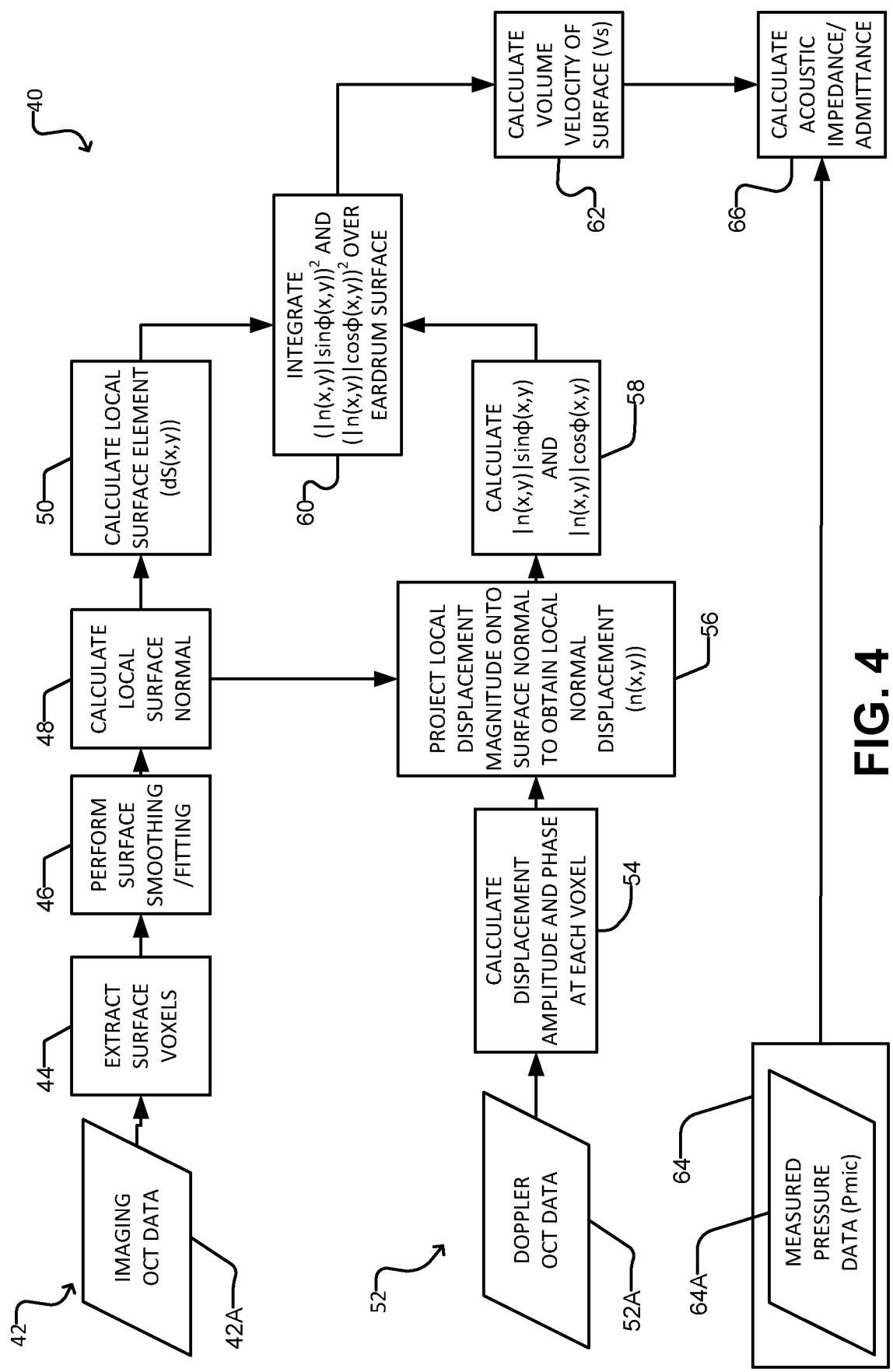
FIG. 4 is a flowchart illustrating a method for calculating impedance according to an example embodiment of the invention.

Referring to FIG. 4, the following description explains an example method 40 for a typical application in which a sound stimulus is delivered to ear 22 while the 3D structure and vibrational response of eardrum 22B are monitored using OCT. The sound stimulus may, for example, have a magnitude of 90 dBSPL at 500 Hz. With the typical vibration signal-to-noise ratio observed in patients, scanning the full surface of eardrum 22B may be completed in less than one minute using this technique.

Method 40 contains two paths which may be performed simultaneously: path 42 for processing structural imaging OCT data 42A, and path 52 for processing Doppler OCT data 52A.

For each voxel within the middle ear, including those on eardrum 22B, the measurement provides a magnitude z(x, y, d) and phase of displacement $\phi(x, y, d)$ in response to the stimulus. x and y are coordinates describing the lateral location of the OCT beam for a line in the image while d is a coordinate describing the depth of a voxel along the line. x and y are not necessarily equally spaced in space. For example, the lateral distance between adjacent voxels may change with depth.

In path 42, at step 44, the voxels on the surface of eardrum 22B are determined along each image line. This may be done by raycasting. A ray is cast along the image line until the first pixel whose intensity in the structural image exceeds a heuristically-determined threshold is encountered. The depth of the first eardrum 22B voxel along the ray is recorded along with the optical beam location and angle for that line in the scan. This provides a set of voxels describing the shape of eardrum 22B.

At step 46, the 2D surface of eardrum 22B will generally be smooth and can be accurately fit using techniques such as parametric fitting of which polynomial least-squares fitting is an example. In addition or in the alternative, a smoothing algorithm can be used to remove noise from the data. In either case, the data yields a smooth 2D surface parametrized only by the coordinates (x, y) since the d coordinate is determined from the raycasting operation.

On path 52, at step 54, the Doppler vibration displacement amplitude |z(x,y)| and phase $\phi(x, y)$ for each voxel on the surface of eardrum 22B can be obtained from the OCT Doppler dataset 52A. This may be achieved, for example, by interpolating using the measured Doppler magnitude and phase for those voxels lying on the surface of eardrum 22B.

From the structural information obtained from the image, the local surface normal vector for the surface of eardrum 22B is constructed at step 48. If a parametric model of eardrum 22B was obtained during the previous steps, this model can be used to calculate the surface normal. Otherwise, the surface normal can be calculated numerically using, for example, a gradient kernel. The surface of eardrum 22B can be assumed to displace along the local normal vector and so the measured displacement, which is the projection of the displacement along the optical axis at scan coordinates x,y can be corrected by dividing it by the cosine of the angle between the normal and optical line direction. If this angle is very close to 90° then regularization may be applied to prevent noise from dominating the measurement. This calculation produces, at step 56, a displacement n(x,y) normal to the surface of eardrum 22B for every voxel on the surface.

For a sound stimulus at angular frequency ω, the instantaneous displacement $n(x,y)e^{-i\omega t}$ of a voxel located at coordinates (x,y) on eardrum 22B is related to the instantaneous velocity $u(x,y)e^{-i\omega t}$ by:

$$u(x,y) = -i\omega n(x,y) \quad (2)$$

The instantaneous volume velocity of the entire eardrum 22B can be expressed as an integral over the individual displacements of surface elements on the tympanic membrane:

$$V_s(t) = -i\omega \oiint |n(x,y)|\cos(\omega t + \phi(x,y))dS(x,y) \quad (3)$$

In the above integral, the area element dS(x,y), as calculated in step 50, is a function of the scanning coordinates x,y because the geometry of the eardrum is generally curved. As the vibrations are small (~100 s of nm at 90 dBSPL) compared to the eardrum thickness (typically 100-300 μm), the tympanic membrane can be considered a thin membrane and almost all of the volume displacement will be due to motion normal to the local membrane surface of eardrum 22B.

At steps 60 and 62, the root-mean-squared (RMS) volume velocity can be calculated as:

$$V_S = -i\omega\sqrt{\frac{1}{T}\int_0^T dt[\oiint |n(x,y)|\cos(\omega t + \phi(x,y))dS(x,y)]^2} \quad (4)$$

where T is the scanning period of laser 12.

Performing the time integration over one period results in the simplified expression:

$$V_S = -i\omega\sqrt{[\oiint |n(x,y)|\cos(\phi(x,y))dS(x,y)]^2 + [\oiint |n(x,y)|\sin(\phi(x,y))dS(x,y)]^2} \quad (5)$$

where |n(x, y)| cos $\phi$(x,y) and |n(x, y)| sin dS(x,y) are quantities that can be calculated, at step 58, at each voxel x, y on the surface of eardrum 22B from the Doppler data. Similarly, the voxel normal surface area dS(x, y) is calculated at step 50 for each scan location x, y, taking into account the surface orientation relative to the scan direction. The integrals $\oiint |n(x, y)| \cos \phi(x, y) dS(x,y)$ and $\oiint |n(x, y)| \sin \phi(x, y) dS(x,y)$ can then be calculated by numerical integration over the surface of eardrum 22B.

If a pressure 64A, e.g. an RMS pressure $P_{RMS}$ is simultaneously recorded with microphone 26, at step 64, the impedance looking into eardrum 22B can be calculated at step 66 as:

$$Z = \frac{P_{RMS}}{V_S} \quad (6)$$

The impedance obtained in this way is an equivalent measure to measures yielded by traditional impedance measurement techniques. The immitance, structural imaging OCT data 42A and/or Doppler OCT data 52A may be displayed on a display, stored in a data store, printed and/or otherwise made available for reference.

ALTERNATIVE EMBODIMENTS

Methods as described herein may optionally be used with data from other measurement techniques that provide spatially-resolved measurements of the motion of the surface of eardrum 22B and sources combined with structural information about the geometry of eardrum 22B in addition to or in place of OCT data. For example, LDV is a technique that may be used to measure spatially resolved motion of eardrum 22B. If combined with data about the geometric structure of eardrum 22B, which could, for example, be obtained from a computed tomography scan, an ultrasound scan, a magnetic resonance imaging scan, or image processing techniques that construct a 3D model from multiple 2D images, the methods disclosed here for OCT could also be applied to obtain acoustic immittance measurements from LDV data.

The sound stimulus from speaker 20 has been described above as being sinusoidal. This is convenient in order to obtain an RMS sound pressure level and vibration level. However, other types of stimulus can be used to obtain acoustic immittance measurements. For example broadband stimuli such as clicks (impulses), white noise, or signals consisting of the sum of sine waves at multiple frequencies may optionally be used to obtain acoustic immittance at multiple frequencies simultaneously. In such approaches a Fourier transform can be applied to the measured sound pressure signal and vibration signal and a ratio of, for instance, the Fourier transform of the pressure to the Fourier transform of the vibration give the impedance as a function of frequency. When click trains, noise, or other broadband stimuli are used, the sweep clock is synchronized to the beginning of the excitation signal to allow averaging over multiple presentations. When sine waves at multiple frequencies are presented simultaneously, the sweep clock is synchronized to the phase of the lowest frequency component of the excitation signal. The use of sinusoidal stimulus signals generally results in a better signal-to-noise ratio at the measured frequencies than can be obtained with broadband stimuli in a given amount of time.

In many ears, part of eardrum 22B is obscured by the scutum. In such cases the volume displacement may be extrapolated based on the motion of the portion of eardrum 22B that can be observed. The fraction of eardrum 22B that is obscured can be estimated from the anatomy and the measured volume velocity may then be scaled up by a factor determined by calibration against standard tympanometry on a population of ears.

In some embodiments the imaging head may comprise a handheld endoscope with a disposable speculum, similar to an otoscope, that is inserted into ear canal 22A. This type of endoscope is convenient because the clinician can use real-time feedback from imaging to obtain a good alignment of the imaging head. One or more tubes may be integrated into the endoscope to carry the acoustic stimulus, connect to microphone 26 and/or deliver a static pressure to ear canal 22A. When a seal is required, a foam or silicone sheath can be placed around the speculum in order to seal ear canal 22A when the speculum is inserted. Controls (e.g. buttons and a selection wheel) may be incorporated into the endoscope to allow the clinician to select different imaging and measurement modes and to switch between B-mode, volumetric, and Doppler imaging; perform tympanometry and an acoustic reflex measurement; or perform a middle ear reflectance measurement. In other embodiments the imaging head may be integrated into a surgical microscope. In yet other embodiments the imaging head may be fixed to a frame used to stabilize the patient's head.

Apparatus as described herein may be applied, for example, by otologists and audiologists. The apparatus may, for example, be applied in clinical settings and intrasurgical applications.

While, in the preferred embodiment, OCT is performed using a swept-source laser 12, in other embodiments, OCT is performed using a broadband light source and spectral-domain OCT. In yet other embodiments, OCT is performed using a broadband light source and time-domain OCT.

In some embodiments light is delivered to eardrum 22B using a rigid endoscope inserted into ear canal 22A. In some embodiments light is delivered to eardrum 22B using a flexible endoscope inserted into ear canal 22A. In some embodiments light is carried to eardrum 22B through free space.

Some embodiments provide one or more of the following advantages:
  The sound source does not require calibration.
  The method may optionally be performed in an open ear canal.
  Imaging of the middle ear may be performed at the same time as measurements are taken.
  The method permits acoustic impedance measurements which use spatial information.
These advantages are explained in more detail below.

The Method is Calibration-Free.

In conventional impedance measurement the sound source must be regularly calibrated in order to know its output impedance and obtain accurate measurement results. Calibration errors can lead to measurement inaccuracy. By measuring volumetric velocity directly, the need for a calibrated source is removed.

The Method can be Performed with an Open Ear Canal.

Conventional middle ear power analysis and tympanometry both require that the ear canal be sealed to obtain accurate measurements. This introduces an extra source of variability as the quality of the seal might differ for different ear canal shapes and with the experience of the operator. The seal can also make the procedure uncomfortable. If eardrum motion is measured directly, the ear canal does not have to be sealed. If it is desired to emulate classic tympanometry, the ear canal must be sealed in order to maintain a desired static pressure, even when making an OCT impedance measurement. In this case the seal is only required for the static pressure, not the impedance measurement.

The Method Allows Imaging to be Performed Simultaneously.

Because conventional impedance measurements require an ear canal seal, the clinician cannot simultaneously image the ear and perform an impedance measurement. With OCT-based impedance measurements, image information comes in throughout the measurement in real-time. This allows the location and motion of all structures in the middle ear to be observed throughout the test, providing information of potentially high diagnostic value. An excellent example of this is that during an acoustic reflex threshold test performed using OCT-based impedance measurements, one would observe, in addition to the increased impedance seen from the ear canal, the actual motion of the ossicles caused by the reflex action in the imaging data. This may prove to be a more reliable indicator of reflex than traditional tests.

The Method Allows Extending Acoustic Impedance Measurements to Make Use of Spatial Information:

Traditional methods of impedance measurement provide a single number for the impedance seen at the ear canal. Effectively this single number takes into account the integrated volume displacement over the entire eardrum. Because Doppler OCT provides spatially resolved displacements, it becomes possible to look at only the volume displacement over a portion of the eardrum. In particular, the eardrum only connects to the ossicular chain at the umbo which represents about 20% of the eardrum surface. An OCT-based impedance measurement could report an impedance obtained by considering only the volume displacement of this portion of the eardrum. This may provide increased sensitivity to ossicular disorders as compared to conventional approaches. In some embodiments the location of the umbo or other selected region of the eardrum is determined automatically by processing images acquired by the apparatus (e.g. OCT images or images by another imaging modality) and/or by processing the Doppler OCT data. In other embodiments the location of the umbo or other region of interest on the eardrum may be input by a user using a suitable user interface.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors. As another example, some or multiple steps in the described methods may be performed by configurable or fixed logic circuits such as a FPGA. The FPGA may, for example, be configured to compute Fourier transforms of OCT data among other functions.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration.

These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

REFERENCES

[1] S. E. Voss and J. B. Allen, "Measurement of acoustic impedance and reflectance in the human ear canal," *J. Acoust. Soc. Am.*, vol. 95, no. 1, pp. 372-384, January 1994.
[2] C. A. of Audiology, "The Value of Acoustic Reflexes in Practice: A Retrospective Look," *Can. Audiol.*, vol. 1, no. 2.
[3] "Impedance Audiometry: Overview, Indications, Contraindications," December 2016.
[4] D. MacDougall, J. Farrell, J. Brown, M. Bance, and R. Adamson, "Long-range, wide-field swept-source optical coherence tomography with GPU accelerated digital lock-in Doppler vibrography for real-time, in vivo middle ear diagnostics," *Biomed. Opt. Express*, vol. 7, no. 11, p. 4621, November 2016.

What is claimed is:

1. A system comprising:
an audio source configured to deliver a sound stimulus within an ear canal for inducing motion of an eardrum at one or more frequencies;
a combined structural and Doppler optical coherence tomography imaging system configured to obtain structural optical coherence tomography data and Doppler optical coherence tomography data characterizing a surf ace of the eardrum, and to measure spatially resolved displacement phase and amplitude values characterizing motion of the surface of the eardrum in response to the applied sound stimulus; and
a processor configured to:
process the structural optical coherence tomography data to determine local surface normal vectors associated with the surface; and
employ the spatially resolved displacement amplitude and phase values, the local surface normal vectors, and the one or more frequencies of the applied sound stimulus to calculate a volume velocity associated with volume displacement normal to the surface of the eardrum;
wherein the processor is further configured such that prior to calculating the volume velocity, the spatially resolved displacement amplitudes are corrected based on the respective local surface normal vectors.

2. The system according to claim 1 wherein the volume velocity, at a given frequency, is obtained by employing the spatially resolved displacement amplitude and phase values, the local normal surface vectors and the given frequency to calculate a local velocity normal to the surface of the eardrum, and integrating the local velocity over the surface of the eardrum to obtain the volume velocity associated with the motion of the eardrum.

3. The system according to claim 2 wherein the system further comprises a microphone operable to measure a pressure of the sound stimulus on the surface, and wherein the processor is further configured to process the volume velocity and the measured pressure to calculate an acoustic impedance.

4. The system according to claim 3 comprising a device for applying a quasi-static pressure to the ear canal and an earpiece that creates an acoustic seal with the ear canal wherein the system is configured to report a change in the volume velocity or acoustic impedance as the quasi-static pressure is varied.

5. The system according to claim 3 wherein the audio source is configured such that the sound stimulus is operative to elicit an acoustic reflex response, and wherein the system is configured to measure a change in the acoustic impedance resulting from the acoustic reflex response.

6. The system according to claim 3 wherein the system is configured to monitor a decay in an acoustic impedance change caused by the acoustic reflex over time.

7. The system according to claim 3 wherein the processor is further configured such that, prior to calculating the acoustic impedance, the following operations are performed:
processing image data collected by the optical coherence imaging system to determine a fraction of the eardrum that has been obscured during image acquisition; and
employing the fraction to scale the measured volume velocity to compensate for the obscured fraction of the eardrum.

8. The system according to claim 2 wherein the audio source is configured such that the sound stimulus is operative to elicit an acoustic reflex response, the system configured to measure motion of at least one of a malleus, incus, stapes and stapedius tendon when the acoustic reflex response is active.

9. The system according to claim 5 wherein the sound stimulus is sinusoidal.

10. The system according to claim 5 wherein the sound stimulus is a broadband stimulus.

11. The system according to claim 10 wherein the broadband stimulus comprises one of clicks, white noise and signals comprising a sum of sine waves at multiple frequencies.

12. The system according to claim 1 comprising a pump controllably coupled to the processor, the pump configured to maintain a static pressure in the ear canal.

13. The system according to claim 1 wherein the optical coherence tomography imaging system comprises one of a swept-source laser and a broadband light source.

14. The system according to claim 13 wherein the swept-source laser is synchronized with a sweep clock signal, the sweep clock signal synchronizing the laser with an acoustic phase of the sound stimulus.

15. The system according to claim 1 wherein the processor is configured to process signals from an interferometer to produce an interferogram representing one or both the ear canal and the surface.

16. The system according to claim 15 wherein the processor is configured to extract structural optical coherence tomography data from a computed magnitude of a discrete Fourier transform of the interferogram.

17. The system according to claim 16 wherein the processor is configured to extract Doppler optical coherence tomography data from the interferogram.

18. The system according to claim 1 wherein the processor is configured to calculate the volume velocity by:
determining a plurality of voxels lying on the surface using the structural optical coherence tomography data;
employing the structural optical coherence tomography data to determine a local surface normal vector for each voxel;
determining vibration displacement amplitude and phase for each of the plurality of voxels using the Doppler optical coherence tomography data;
employing the vibration displacement amplitude, phase and the local surface normal vector of each voxel to determine a plurality of spatially resolved individual velocities normal to the surface, each of the plurality of individual velocities corresponding to an individual velocity of one of the plurality of voxels normal to the surface, induced by the sound stimulus; and
integrating over the plurality of spatially resolved individual velocities.

19. The system according to claim 18 wherein the plurality of voxels corresponds to a portion of the surface that includes an umbo at which a tympanic membrane is coupled to an ossicular chain of an ear.

20. A system for measuring an acoustic impedance of a middle ear of an ear, the system comprising:
an audio source operable to generate a sound stimulus, the sound stimulus effective to induce motion of an eardrum of the ear at one or more frequencies;
a combined structural and Doppler optical coherence tomography imaging system configured to obtain structural optical coherence tomography data characterizing a surface of the eardrum, and to measure displacement amplitude and phase values at points of a two-dimensional array of points on the eardrum in response to the sound stimulus;
a microphone operable to measure pressure of the sound stimulus on the ear drum; and
a processor, the processor configured to:
process the structural optical coherence tomography to determine local surface normal vectors associated with the surface; and
employ the displacement amplitude and phase values, the local surface normal vectors, and the one or more frequencies of the applied sound stimulus to calculate a volume velocity associated with volume displacement normal to the surface of the eardrum; and
calculate the acoustic impedance of the middle ear as a ratio of the measured pressure of the sound stimulus on the ear drum to the volume velocity;
wherein the processor is further configured such that prior to calculating the volume velocity, the spatially resolved displacement amplitudes are corrected based on the local surface normal vectors.

21. A method comprising:
inducing motion of an eardrum by applying a sound stimulus to the eardrum at one or more frequencies;
with a combined structural and Doppler optical coherence tomography imaging system, imaging a surface of the eardrum to obtain structural optical coherence tomography data characterizing a surface of the eardrum and measure spatially-resolved displacement phase and amplitude values characterizing motion of the surface of the eardrum in response to the applied sound stimulus; and
by an electronic data processor, processing the structural optical coherence tomography to determine local surface normal vectors associated with the surface and employing the spatially resolved displacement amplitude and phase values, the local surface normal vectors, and the one or more frequencies of the applied sound stimulus to calculate a volume velocity associated with volume displacement normal to the surface of the eardrum;
wherein, prior to calculating the volume velocity, the spatially resolved displacement amplitudes are corrected based on the respective local surface normal vectors.

22. The method according to claim 21 wherein the system further comprises a microphone operable to measure a pressure of the sound stimulus on the surface, and wherein the processor is further configured to process the volume velocity and the measured pressure to calculate an acoustic impedance.

23. The method according to claim 22 further comprising, prior to calculating the acoustic impedance, performing the following steps:
processing image data collected by the optical coherence imaging system to determine a fraction of the eardrum that has been obscured during image acquisition; and
employing the fraction to scale the measured volume velocity to compensate for the obscured fraction of the eardrum.

* * * * *

UNITED STATES PATENT AND TRADEMARK OFFICE
CERTIFICATE OF CORRECTION

PATENT NO. : 12,016,680 B2
APPLICATION NO. : 16/753258
DATED : June 25, 2024
INVENTOR(S) : Robert Adamson et al.

It is certified that error appears in the above-identified patent and that said Letters Patent is hereby corrected as shown below:

In the Claims

Claim 1 should read:
1. A system comprising:
an audio source configured to deliver a sound stimulus within an ear canal for inducing motion of an eardrum at one or more frequencies;
a combined structural and Doppler optical coherence tomography imaging system configured to obtain structural optical coherence tomography data and Doppler optical coherence tomography data characterizing a surface of the eardrum, and to measure spatially resolved displacement
phase and
amplitude values characterizing motion of the surface of the eardrum in response to the applied sound stimulus; and
a processor configured to:
process the structural optical coherence tomography data to determine local surface normal vectors associated with the surface; and
employ the spatially resolved displacement amplitude and phase values, the local surface normal vectors, and the one or more frequencies of the applied sound stimulus to calculate a volume velocity associated with volume displacement normal to the surface of the eardrum;
wherein the processor is further configured such that prior to calculating the volume velocity, the spatially resolved displacement amplitudes are corrected based on the respective local surface normal vectors.

Signed and Sealed this
Fifth Day of November, 2024

Katherine Kelly Vidal
*Director of the United States Patent and Trademark Office*